United States Patent [19]

Anthony

[11] Patent Number: 4,679,551
[45] Date of Patent: Jul. 14, 1987

[54] DEVICE FOR PERFORMING THERAPEUTIC TREATMENTS

[75] Inventor: Jean M. Anthony, Antwerpen, Belgium

[73] Assignee: Tomtec, N.V., Antwerpen, Belgium

[21] Appl. No.: 704,631

[22] Filed: Feb. 22, 1985

[30] Foreign Application Priority Data

| | | | |
|---|---|---|---|
| Feb. 23, 1984 | [BE] | Belgium | 2/60347 |
| Mar. 26, 1984 | [BE] | Belgium | 2/60374 |
| Apr. 25, 1984 | [BE] | Belgium | 2/60398 |
| Oct. 23, 1984 | [BE] | Belgium | 0/213872 |

[51] Int. Cl.$^4$ ................ A61B 19/00; A61M 35/00
[52] U.S. Cl. ............................. 128/67; 604/19;
604/289; 604/296; 128/1 R; 128/200.16
[58] Field of Search ............... 604/289, 296, 19, 22;
128/1, 51, 67, 200.16, 200.14, 204.13

[56] References Cited

U.S. PATENT DOCUMENTS

| | | | |
|---|---|---|---|
| 2,524,720 | 10/1950 | Watrous | 604/289 |
| 3,990,452 | 11/1976 | Murry et al. | 128/305 |
| 4,471,773 | 9/1984 | Bunnell et al. | 128/200.16 |
| 4,551,139 | 11/1985 | Plaas et al. | 604/289 |

OTHER PUBLICATIONS

Acta Anaesth. Scaninau., 1964, 8, pp. 79–95, "Ultrasonic Generation of Aerosol for the Humidification of Inspired Gas During Volume-Controlled Ventilation" Herzog et al.

Primary Examiner—C. Fred Rosenbaum
Assistant Examiner—Gene B. Kartchner
Attorney, Agent, or Firm—Scully, Scott, Murphy and Presser

[57] ABSTRACT

There is described a device for performing therapeutic treatments, such as notably the moistening of the mouth cavity and lips of a comatose or terminal patient, the retaining in a moist and sterile condition of a wound or operating field, which device is formed by an ultrasound sprayer which receives water or a similar liquid from a tank, said ultrasound sprayer can spray droplets the size of which does not exceed 70 microns, and is mounted on the end of a movable arm, in such a way that the spraying may occur in the direct vicinity of the space or area to be treated, while means are provided to prevent with a stoppage of the sprayer operation, the conveying to the patient of condensed water or moisture spray.

6 Claims, 2 Drawing Figures

DEVICE FOR PERFORMING THERAPEUTIC TREATMENTS

Background Of The Invention

This invention relates to a device for performing therapeutic treatments, such as notably the moistening of the mouth cavity and the lips of a comatose or terminal patient, the retaining in a moist and sterile condition of a wound or operating field, as well as the therapeutic treatment of the respiratory tract.

Bed-ridden patients, particularly terminal patients, as well as patients which lie in reanimation, often breath with their mouth open. The drying-out of the lips, the tongue and the pharynx causes in these patients, an extremely painful condition.

To obviate this condition in some way, it has already been proposed to keep those areas moist by using an atomizing apparatus, to replace the human agency.

The apparatus generally used for this purpose, are devices such as evaporators which generate by means of ultrasound waves, generate a mist or spray which is conveyed to that location where said mist or spray is to be used. As the ultrasound sprayer operates some distance away from said location, the use of a fan is required to move the mist through a tube. An air filter and a bacteria filter the sterile action of which is open to question, are thereby also required. The supply of mist or spray may never be stopped without condensing occuring inside said tube. Now it is precisely a requirement that the spray or mist has to meet strict conditions, as well as the device which supplies said spray. Mostly the moistening of the mouth cavity and the lips of a comatose patient brings very high requirements. For instance, the spraying may not cause any moisture accumulation in or about the pharynx, because this causes in such patients a swallowing reflex. Such a swallowing reflex may have, under such conditions, very severe consequences. This means that spraying may only be used when the same may be very strictly programmed and causes no moisture or water accumulation.

Another requirement is that the spray or mist should reach a well-defined space or area, and that the immediate surroundings of such location, for example the bedding or bed-linen, should not be moistened.

SUMMARY OF THE INVENTION

To obtain such a result according to the invention, the device is formed by an ultrasound sprayer which receives water or a similar liquid from a tank, which ultrasound sprayer can spray droplets the size of which does not exceed 70 microns, and said sprayer is mounted on the end of a movable arm, in such a way that the spraying may occur in the direct vicinity of the area or space to be treated, while means are provided to prevent with a stoppage of the sprayer operation, the conveying to the patient of condensed water or moisture, mist or spray.

Still according to the invention, said means are formed by an unit comprising a tube, a valve mounted in said tube which is controlled by a programmed time switch, which time switch stops the ultrasound sprayer operation after said valve has been closed by said same time switch, whereby the inner cross-section of said tube is so selected that when said valve is closed, due to the capillary action, no water or similar liquid flows to said ultrasound sprayer.

Brief Description of the Drawings

Other details and advantages of the invention will stand out from the following description, given by way of non limitative example and with reference to the accompanying drawings, in which.

Detailed Description of the Preferred Embodiments

Figure 1:
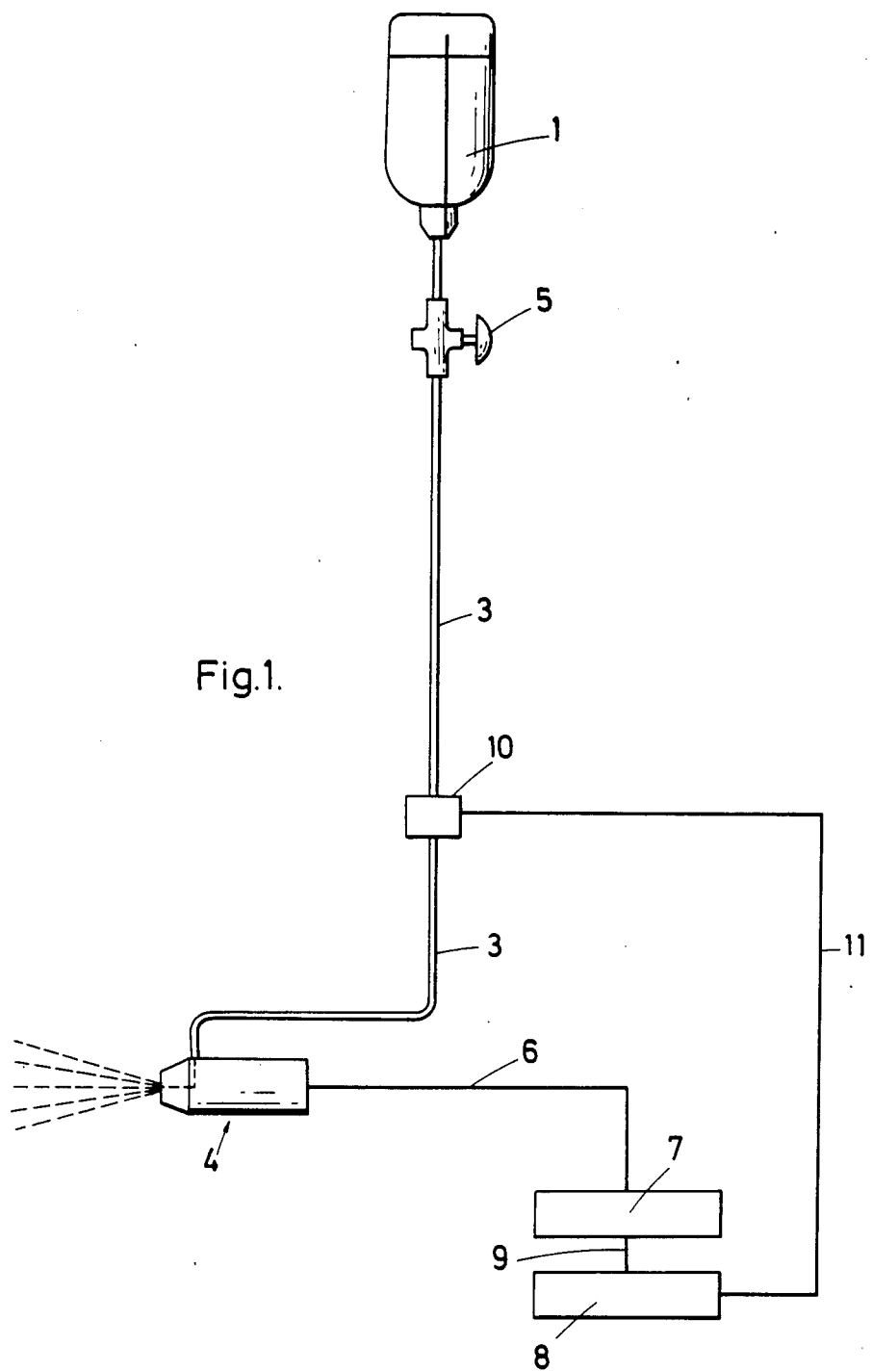
FIG. 1 is a diagrammatic drawing of the essential components of the device according to the invention.
Figure 2:
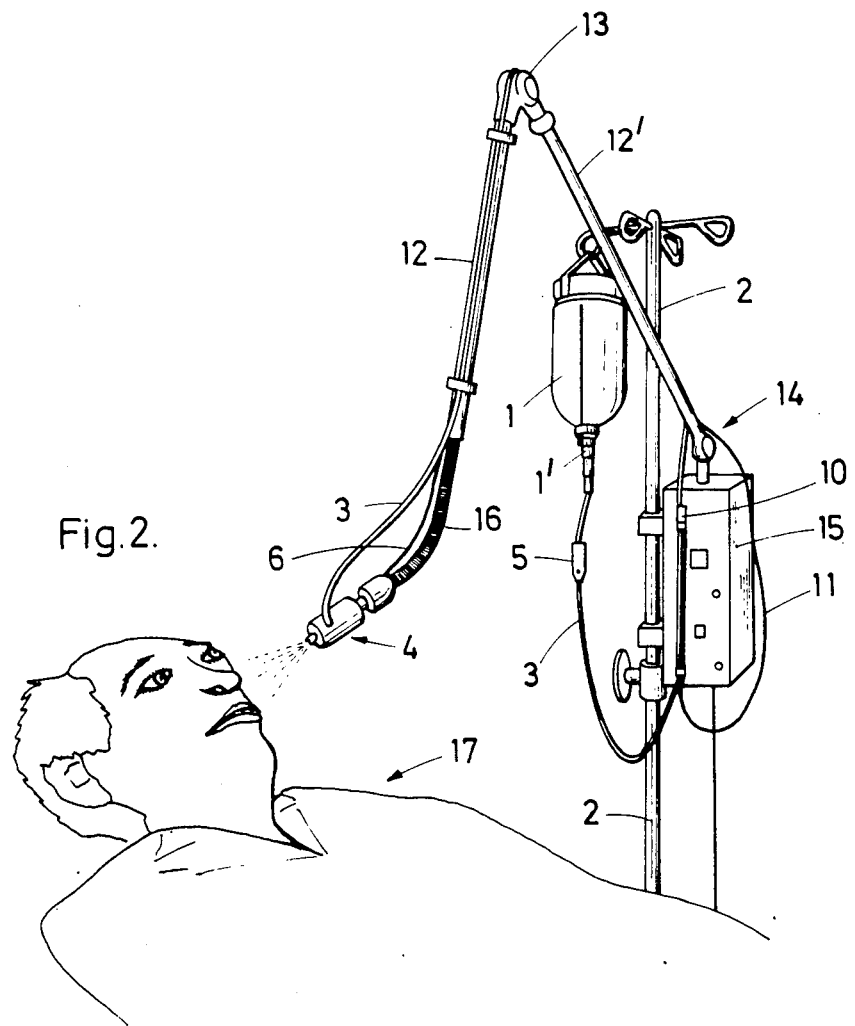
FIG. 2 shows on another scale, in a perspective view the way the device according to the invention may be used.

The device as shown in said figures comprises a tank 1 or bottle with drop counter 1', which is hung from a stand 2 (FIG. 2). The tank contains water or some similar liquid which flows through a tube 3 in the direction of the ultrasound sprayer 4. On the tube is mounted a conventional hand-operated regulating cock 5. The ultrasound sprayer 4 is connected through a coaxial cable 6 to the ultrasound generator 7.

A time switch 8 is connected to the ultrasound sprayer 4 through a cable 9, and to a valve 10 mounted on tube 3, through a cable 11.

The valve 10 is for example an electromagnetic valve through which runs tube 3 and which closes said tube by pinching. When said electromagnetic valve is activated, tube 3 is open. The flowing of water or some similar liquid is thus made possible during activation of tube 3. When the power fails, the valve remains closed and there is no danger of leaking.

The inner cross-section of tube 3 is so selected that after closing of electromagnetic valve 10, due to the capillary action, the further flowing of water or similar liquid in the direction of the ultrasound sprayer 4, is immediately stopped.

The time switch 8 is programmed to fulfill a threefold function. The programmed time switch 8 first controls the working cycle of the ultrasound sprayer. In the second place, the time switch controls the opening time of valve 10, and finally the working time of the ultrasound sprayer.

The programming of said two last operations is so adjusted that the closing of valve 10 always precedes the stopping of the ultrasound sprayer 4. This is indeed very important as thereby the spraying of water from tube 3 always occurs according to the required standards. The forming of large drops which causes the above-described swallowing reflex of the patient, is thus strictly avoided. That water or moisture which is present inside the sprayer after closing of valve 10 is sprayed completely in the form of mist or spray with the required size.

When the water does not flow by gravity to the sprayer 4, said water may be pumped through tube 3.

It is very characteristic of the invention that due to the arrangement of the various elements in the unit and the way the time switch is programmed, the feeding of water to the ultrasound sprayer is always cut-off before the sprayer operation is stopped. There results therefrom that the ultrasound sprayer 4 atomizes all the available water, which prevents large water drops from forming at the end of the spraying process.

Due to the mist or spray structure, the moistening of a define space or area is achieved without moistening the surrounding bedlinen or bedding. The moistening of the mouth cavity and the lips may occur when necessary without making use of a mask.

The spraying process, which does not allow, as already stated hereinabove, the forming of large drops, may be adapted to the patient breathing rhythm. The synchronizing of the atomizing time with the breathing is easily achieved by means of the time switch program. The remote-controlling of said structures is naturally very simple. In many cases, the patient himself may also intervene, but however only on the cycle. This means that in all circumstances, the atomizing occurs under excellent conditions, as the flowing of large drops is strictly avoided because the atomizer, which provides the available moisture, is always cut-off after the closing of valve 10. It is possible under the same advantageous conditions as already stated above, to treat an operating field with sterile moisture. The same is true for organs, and in particular with open-heart surgery. The device differs, as may be deduced from the above description, from the known apparatus due to strictly controlled amounts atomized moisture always being fed without any danger of forming large drops the disadvantageous structure of which is known.

Some further details will now be described with reference to FIG. 2. It may be seen from this figure that the sprayer 4 is mounted on the end of an adjustable hinged arm 12—12'. Said hinged arm 12—12' has a first hinge connection 13 and a second one 14. By means of the hinge connection 14, the arm 12' may be adjusted to a desired angle relative to the housing 15, which may be adjusted to a preferred height relative to stand 2. The housing 15 bears the programmed time switch 8 and the microcomputer-controlled components, such as notably the ultrasound generator 7. Inside the housing are also provided the required current transformer, operating elements and control lights. Between the ultrasound sprayer 4 and arm 12, a flexible arm 16 is provided whereby said sprayer 4 may be adjusted in various positions relative to a patient who is shown in 17 in FIG. 2.

In every circumstance, the sprayed moisture reaches the patient with a minimized moisture loss. The apparatus is particularly economical due to the sequence of working thereof.

It is to be noted with regards to the sterility of all the components, same may be designed as throwaway components. They are thereby easy to remove and thus easy to sterilize, this being notably the case for the ultrasound sprayer.

I claim:

1. Apparatus for moistening a body area of a patient, comprising:
    holding means to hold a supply of a liquid;
    ultrasonic spray means having an activated state to spray the liquid onto the body area, and a deactivated state wherein the spray means does not spray the liquid onto the body area;
    liquid conducting means connected to the holding means and to the ultrasonic spray means, and having an open position to conduct liquid from the holding means to the ultrasonic spray means, and a closed position to prevent the liquid from passing from the holding means to the ultrasonic spray means; and
    control means connected to the liquid conducting means to regularly move the liquid conducting means between the open and closed positions a plurality of times during a pre-determined interval, and further connected to the ultrasonic spray means to regularly change said ultrasonic spray means between the activated and deactivated states a plurality of times during the predetermined interval, the control means maintaining the ultrasonic spray means in the activated state for a brief period each time after the liquid conducting means is moved from the open position to the closed position during the predetermined interval, to inhibit the accumulation of fluid in the ultrasonic spray means when said ultrasonic spray means is in the deactivated state.

2. Apparatus according to claim 1, wherein:
    the liquid conducting means includes
    (i) a tube connected to the holding means and the ultrasonic spray means to conduct fluid to said spray means from the holding means, and
    (ii) a valve mounted in the tube, and having an open position to conduct liquid through the tube to the ultrasonic spray means, and a closed position to prevent the liquid from passing through the tube from the holding means to the liquid conducting means,
    the tube having an inside surface stopping liquid from flowing through the tube to the ultrasonic spray means when the valve is in its closed position; and
    the control means includes a programmed time switch connected to the valve to move the valve between its open and closed position, and further connected to the ultrasonic spray means to selectively change the ultrasonic spray means between the activated and deactivated states, the programmed time switch maintaining the ultrasonic spray means in the activated state for a brief period each time after the valve is moved to its closed position.

3. Apparatus according to claim 2, wherein, when the valve is in its open position, liquid is drawn by gravity from the holding means, through the tube, and to the ultrasonic spray means.

4. Apparatus according to claim 2, further comprising a pump to pump the liquid from the holding means, through the tube, and to the ultrasonic spray means.

5. Apparatus according to claim 1 wherein:
    the ultrasonic spray means includes a transducer having an activated state to spray the liquid onto the body area, and a deactivated state wherein the spray means does not spray the liquid onto the body area; and
    the control means includes means to change the transducer between its activated and deactivated states in synchronization with the patient's breathing.

6. Apparatus according to claim 1, further comprising:
    a support stand; and
    means connecting the ultrasonic spray means to the support stand for movement through a range of positions, and to hold the ultrasonic spray means in a multitude of different positions in said range, the connecting means including
    (i) a housing connected to the support stand, the height of the housing being adjustable along said support stand,
    (ii) a first arm pivotally connected to the housing,
    (iii) a second arm pivotally connected to the first arm, and
    (iv) means connecting the ultrasonic spray means to the second arm for movement therewith.

* * * * *